United States Patent [19]

Duncan

[11] Patent Number: 5,601,609

[45] Date of Patent: Feb. 11, 1997

[54] IMPLANTABLE CARDIAC STIMULATING DEVICE AND METHOD FOR ADMINISTERING SYNCHRONIZED CARDIOVERSION SHOCK THERAPY TO PROVIDE PREEMPTIVE DEPOLARIZATION

[75] Inventor: James L. Duncan, Alpharetta, Ga.

[73] Assignee: Pacesetter, Inc., Sylmar, Calif.

[21] Appl. No.: 403,593

[22] Filed: Mar. 14, 1995

Related U.S. Application Data

[63] Continuation-in-part of Ser. No. 123,025, Sep. 15, 1993, abandoned.

[51] Int. Cl.$^6$ .................................................... A61N 1/362
[52] U.S. Cl. .................................................. 607/5; 607/14
[58] Field of Search ........................................ 607/4, 5, 14

[56] References Cited

U.S. PATENT DOCUMENTS

| | | |
|---|---|---|
| 3,942,534 | 3/1976 | Allen et al. ............................ 607/14 |
| 4,163,451 | 8/1979 | Lesnick et al. . |
| 4,280,502 | 7/1981 | Baker, Jr. et al. . |
| 4,312,356 | 1/1982 | Sowton et al. . |
| 4,384,585 | 5/1983 | Zipes . |
| 4,390,021 | 6/1983 | Spurrell et al. . |
| 4,398,536 | 8/1983 | Nappholz et al. . |
| 4,406,287 | 9/1983 | Nappholz et al. . |
| 4,408,606 | 10/1983 | Spurrell et al. . |
| 4,427,011 | 1/1984 | Spurrell et al. . |
| 4,541,430 | 9/1985 | Elmqvist .............................. 607/14 |
| 4,587,970 | 5/1986 | Holley et al. . |
| 4,662,377 | 5/1987 | Heilman et al. . |
| 4,787,389 | 11/1988 | Tarjan . |
| 4,788,980 | 12/1988 | Mann et al. .......................... 607/14 |
| 4,790,317 | 12/1988 | Davies . |
| 4,830,006 | 5/1989 | Haluska et al. . |
| 4,869,252 | 9/1989 | Gilli . |
| 4,875,483 | 10/1989 | Vollmann et al. . |
| 4,895,151 | 1/1990 | Grevis et al. . |
| 4,989,602 | 2/1991 | Sholder et al. . |
| 4,998,974 | 3/1991 | Aker . |
| 5,063,928 | 11/1991 | Grevis et al. . |
| 5,083,562 | 1/1992 | de Coriolis et al. . |
| 5,184,615 | 2/1993 | Nappholz et al. ....................... 607/4 |

OTHER PUBLICATIONS

Zipes et al., "Early Experience with an Implantable Cardioverter", N. E. Journal of Med. voll 311, Aug. 23, 1984 No. 8.

Primary Examiner—Jeffrey R. Jastrzab
Attorney, Agent, or Firm—Lisa P. Weinberg

[57] ABSTRACT

An implantable cardioversion shock therapy system is provided which delays delivery of a cardioversion shock until late in the cardiac cycle to optimize the chance for the vast majority of ventricular myocardial tissue to be non-refractory. The system in intended to increase efficacy and safety by properly synchronizing the cardioversion shock to the appropriate portion of the cardiac cycle to successfully terminate a tachycardia episode. The timing of the cardioversion shock is programmable as either a percentage of measured tachycardia cycle length or fixed delay in milliseconds.

31 Claims, 3 Drawing Sheets

IMPLANTABLE CARDIAC STIMULATING DEVICE AND METHOD FOR ADMINISTERING SYNCHRONIZED CARDIOVERSION SHOCK THERAPY TO PROVIDE PREEMPTIVE DEPOLARIZATION

This is a continuation-in-part of application Ser. No. 08/123,025 filed on Sep. 15, 1993, now abandoned.

FIELD OF THE INVENTION

The present invention relates to implantable cardiac stimulation devices that provide cardioversion shock therapy for interrupting episodes of tachycardia. More particularly, the present invention relates to specific improvements to such devices that (i) reduce the potential for lethal acceleration, (ii) increase the probability that the treatment will safely terminate the arrhythmia, and (iii) allow cardioversion therapy to use a lower energy electrical stimulation pulse, thereby lowering power consumption of the devices and reducing discomfort to patients.

BACKGROUND OF THE INVENTION

One form of cardiac arrhythmia with serious consequences is tachycardia. Tachycardia is a condition where an abnormally high heart rate severely affects the ability of the heart to pump blood. The higher the heart rate, the more dangerous the condition. In ventricular tachycardia (VT), the QRS complexes defining the heart rate are abnormally broad and occur at a rate in the range from about 100 to about 250 beats per minute. Sustained episodes of VT are particularly dangerous because they may deteriorate into ventricular fibrillation (VF), the most life-threatening cardiac arrhythmia. VF is the result of disordered, rapid stimulation of ventricular cardiac tissue, which prevents the ventricles from contracting in a coordinated fashion. VF may cause a severe drop in cardiac output and death if not quickly reverted.

Tachycardia is often the result of electrical feedback within the heart—a natural beat results in the feedback of an electrical stimulus which prematurely triggers another beat. Tachycardia control is frequently achieved by applying electrical stimulation to the heart. The application of electrical stimulation disrupts the stability of the feedback loop, thereby returning the heart to normal sinus rhythm.

One type of electrical stimulation therapy that is known for interrupting tachycardia is cardioversion shock therapy. Cardioversion shock therapy is performed by applying an electrical shock to cardiac tissue in order to depolarize the ventricular myocardium. This allows the site of fastest spontaneous discharge, typically the sinus node, to regain pacing control, thereby terminating the tachycardia episode. In known cardioversion systems, the cardioversion shock is electronically synchronized to fire at the R-wave following confirmation of the arrhythmia. Because of electronic delays which are the result of device switching and charging requirements, the shock is generally provided shortly after the confirming R-wave. Nevertheless, the shock is often administered while significant portions of cardiac tissue are still refractory from the confirming depolarization. A successful cardioversion shock that is administered while significant portions of cardiac tissue are refractory may require a higher energy content than would otherwise be the case. Also, an improperly timed cardioversion shock can cause an afterdepolarization which can prolong the arrhythmia and even lead to a lethal acceleration.

Another type of electrical stimulation therapy known for interrupting tachycardia is antitachycardia pacing. This type of therapy is typically provided by a pacemaker that delivers antitachycardia pacing pulses to cardiac tissue in a manner intended to revert the tachycardia episode. Antitachycardia pacing pulses are of much lower energy than cardioversion shocks, typically between about 25 μjoules and about 30 μjoules and accordingly, and such pacing pulses should be delivered when the heart is most responsive to external stimulation. More particularly, antitachycardia pacing pulses should be delivered when the heart is non-refractory.

Unfortunately, there is usually no way of knowing exactly when the refractory period associated with the preceding R-wave ends. In recent years, pacemakers that provide antitachycardia pacing therapy have employed various techniques in an attempt to deliver antitachycardia pacing pulses to the portion of the cardiac cycle most likely to lead to termination of the tachycardia episode. For example, U.S. Pat. No. 4,280,502 (Baker et al.) refers to a pacemaker which, after confirmation of a tachycardia episode, automatically initiates a search routine consisting of a sequence of stimulation pulses. The pulses are provided within a predetermined time interval after a confirmation tachycardia beat. The refractory period is estimated from the experimental results of the search routine, and the search is terminated when a normal heartbeat is detected. If the first search routine is unsuccessful at terminating the tachycardia episode, a second pulse is then applied following the previously determined refractory interval by a second interval which is also experimentally determined by a second search routine.

U.S. Pat. No. 4,390,021 (Spurrell et al.) refers to a pacemaker which generates a sequence of two electrical stimulation pulses to terminate tachycardia. The delay of the first stimulation pulse and the coupled delay between the first and the second pulse are each scanned through 16 discrete steps. Successful time delay parameters are permanently stored, and on the next confirmed episode of tachycardia, scanning begins with the most recent successful synchronization parameters.

U.S. Pat. No. 4,587,970 (Holley et al.) refers to a pacemaker which uses experimental data taken from a general sample population to determine a function estimating the relationship between refractory period and heart rate. A sequence of pacing pulses is generated at intervals defined by the predetermined function in an attempt to synchronize the pacing pulses to a time shortly after the end of the refractory period. If the tachycardia episode is not terminated, another sequence of pulses is generated. The rate of the new sequence is decreased or increased depending upon whether an unevoked heartbeat was sensed during the preceding sequence.

U.S. Pat. No. 4,398,536 (Nappholz et al.) refers to a programmable pacemaker which automatically increases the pulse rate. A burst of pulses is generated after the last heartbeat used to confirm tachycardia. The initial time interval between the last heartbeat used to confirm tachycardia and the first pulse in the sequence is equal to a measured heartbeat cycle less a fixed decrement. If tachycardia persists, another pulse burst is generated at a higher rate. After exceeding the maximum rate, the scanning resumes during the next cycle at the minimum rate. The last burst rate which is successful in terminating tachycardia is stored in the pacemaker and is used for the first burst generated following the next tachycardia confirmation.

The features described above have enabled pacemakers capable of providing antitachycardia pacing therapy to interrupt tachycardia. However, this technology is not applicable to implantable cardiac stimulating devices that provide cardioversion shock therapy. Indeed, the aforedescribed approaches taken with respect to antitachycardia pacing devices would be inappropriate for cardioversion shock therapy systems, because they require the generation and delivery of a "sequence" or "burst" of pulses. A sequence or burst of cardioversion shocks, which are typically several orders of magnitude greater in energy content than antitachycardia pacing pulses, would rapidly deplete limited energy reserves, and could possibly cause great discomfort to the patient.

Prior art cardioversion shock systems either provide no synchronization or they synchronize the stimulation pulses to fire immediately after an R-wave (that is, when the tissue is generally refractory), rather than in the period at which the heart is fully responsive to external stimulation (i.e., when the heart is in a repolarized state, or non-refractory state). During the refractory period of the heart, the cardiac muscle is insensitive to restimulation and cannot respond to a stimulus until after most of the repolarization process is completed.

Furthermore, the cardioversion shocks provided by some "synchronized" systems are administered at approximately the same time relative to the confirming R-wave regardless of the patient's heart rate. Since the timing of the repolarization period relative to the previous R-wave is a function of heart rate, these prior art systems that are heart rate independent do not accurately synchronize delivery of cardioversion shocks to the repolarization period. Consequently, these systems may administer shocks while the heart is generally refractory, may require higher than necessary energy content, and may require additional shocks, thereby increasing the possibility of discomfort to the patient and reducing the useful life of the implanted cardioverter.

What is needed, therefore, is an implantable cardiac stimulating device that attempts to administer a cardioversion shock during the period of the cardiac cycle when the heart is primarily repolarized, so that a lower energy cardioversion shock can effectively interrupt a tachycardia episode because the tissue is responsive to an electrical stimulation pulse. A cardioversion shock properly administered when the heart is responsive to an external stimulus, would optimize the chance of eliciting a heartbeat that preempts the next expected tachycardia beat.

SUMMARY OF THE INVENTION

The present invention provides an implantable cardiac stimulating device and a method for synchronizing cardioversion shocks to the heart during a predetermined time interval when the heart is expected to be repolarized.

The implantable cardiac stimulating device of the present invention administers therapy for terminating a tachycardia more effectively and safely than known "synchronous" cardioversion shock therapy systems, which simply synchronize the shocks to the refractory period of the previous R-wave that is used to confirm episodes of tachycardia. In general, the present invention delays the shocks until late in the cardiac cycle, when the heart is expected to be repolarized, thereby optimizing the chance for the vast majority of the ventricular myocardium to be non-refractory.

This invention relates not only to the implantable cardiac stimulating device itself, including the manner in which cardioversion shocks are delivered to the heart, but also to a method of synchronizing the cardioversion shocks to the repolarization period of the cardiac cycle. More particularly, the present invention is directed to providing preemptive cardioversion shock therapy shortly before the tachycardia beat which follows the confirmation so that it falls in the repolarization period of the cardiac cycle.

In a preferred embodiment of the present invention, a cardioversion shock is synchronized to be administered during the repolarization period which follows the refractory period after a confirmation R-wave. While it is possible to determine the end of the refractory period, it would require extra stimuli and a delay in the time-to-termination of the arrhythmia. Instead, the present invention proposes determining a delay period which has a high probability of falling in the repolarization period of the cardiac cycle. Typically, the physician will characterize the patient's various tachycardia rhythms at implant and can easily determine a window which will preempt the various tachycardias. For example, if the patient has tachycardias at a multiplicity of rates, the physician may desire a delay period which also varies as a function of the tachycardia rate, e.g., using a percentage of the measured tachycardia rate. Alternatively, it may be desirable to select a fixed delay, say 300 or 400 ms, after the last R-wave to insure that the cardioversion shock does not occur during a T-wave and accelerate the arrhythmia.

Such a properly synchronized cardioversion shock has a high probability of creating an action potential that is conducted through the heart. If successful in creating an action potential, the cardioversion shock will elicit a heartbeat that preempts the next anticipated tachycardia beat. In this way, the tachycardia episode may be efficiently and safely reverted.

The preferred embodiment of the present invention includes a sensor for monitoring the cardiac signals; an analog-to-digital converter for converting the analog data from the sensor into conventional digital signals; a microprocessor for analyzing incoming sensor data, processing a sequence of stored instructions, and controlling the generation and delivery of shocks; nonvolatile memory for storing control instructions and program data; an internal telemetry stage for sending and receiving data from an external programmer; and a pulse generator for generating cardioversion shocks under control of the microprocessor. The cardioversion shocks are delivered to cardiac tissue by a shocking lead, which may also be used as part of the electrophysiology sensor. Although the invention is described in the context of an implantable device, the principles disclosed herein may also be applied to external cardioversion shock therapy systems.

The present invention provides numerous advantages over prior art cardioversion systems. Potentially less energy is required to successfully revert the tachycardia to sinus rhythm if the cardioversion shock is properly synchronized to the repolarization period of the cardiac cycle. Also, fewer cardioversion shocks may be necessary. In fact, the preferred embodiment of this invention uses only a single cardioversion shock to interrupt a tachycardia episode. The use of fewer, lower amplitude shocks both reduces the discomfort to the patient and increases the useful life of the implantable cardiac stimulating device by using less energy.

In the preferred embodiment, the approach to cardioversion therapy described herein is heart rate dependent. More particularly, the patient's tachycardia rate is measured and utilized to synchronize the cardioversion shock to the repolarization period of the cardiac cycle. This is necessary for proper synchronization, since the timing of the repolarization period is heart rate dependent. The therapy is thus generally applicable to the patient population without the necessity of sophisticated programming.

Also, the preferred embodiment of the present invention provides preemptive cardioversion shock therapy. Specifically, the cardioversion shock is synchronized to the repolarization period of the cardiac cycle, and will thus have a high probability of eliciting a heartbeat that will preempt the next expected tachycardia beat. This is in contrast to the prior art post-arrhythmia systems, which typically synchronize the cardioversion shock to a period of time immediately after the heartbeat used to confirm the tachycardia episode.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which.

DETAILED DESCRIPTION OF THE PREFERRED EMBODIMENTS

For an understanding of the theory behind the invention, it is useful to describe the response of heart tissue to a stimulus, either naturally conducted or artificially stimulated. While the description below is directed generally towards applying a cardioversion stimulation pulse synchronously with the last detected R-wave, it is within the spirit of the invention that the same principles can be applied in the atrium in detecting and cardioverting atrial tachycardia.

Figure 1:
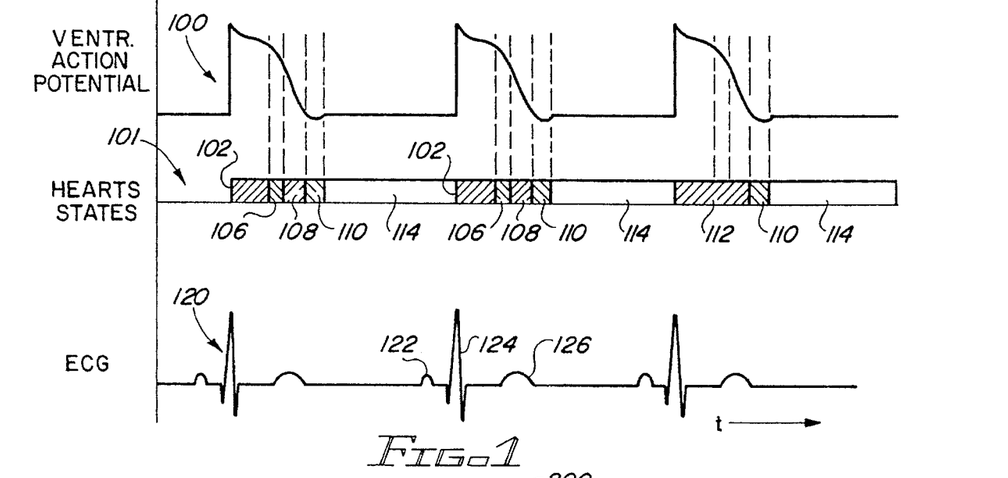
FIG. 1 is a graphical representation of refractory periods of a myocyte and a corresponding surface electrocardiogram (ECG)

FIG. 1 graphically depicts an action potential of a myocyte 100 (i.e., a muscle cell potential as recorded from a microelectrode inserted into ventricular tissue) and a corresponding surface electrocardiogram (ECG) 120, all shown synchronously in time. The surface electrocardiogram 120 represents the summation of all the action potentials generated by the muscle tissue, as seen by electrodes placed on the body's surface. Briefly, the electrocardiogram 120 is composed of a P-wave 122, a "QRS" complex 124, and a T-wave 126. (While the myocyte 100 is shown synchronous in time with the R-wave, the mechanism for depolarization is the same in the atrium.)

FIG. 1 also shows the various heart states 101 corresponding to the myocyte action potential 100. During an absolute refractory period 102, the myocyte (not shown) is nonresponsive to applied stimulation. Thus if a stimulation pulse is applied during the absolute refractory period 102, it will not result in depolarization. An effective refractory period 106 includes a brief period beyond the absolute refractory period 102 during which stimulation may produce a localized depolarization that does not effectively propagate throughout the myocardium. During a relative refractory period 108, stimulation may produce a weak action potential that propagates slowly. The summation of the absolute refractory period, the effective refractory period, and the relative refractory period will hereinafter be referred to as the "total refractory period" 112 of the tissue.

Following the total refractory period 112 is a supranormal period 110 wherein a relatively small stimulus is capable of triggering an action potential. Ideally, cardioversion shock may require a lower shock energy when a stimulation pulse is synchronized to the supranormal period 110. However, in practice, it is difficult to detect the supranormal period without applying a series of stimulation pulses, which series could also accelerate the arrhythmia, particularly if any of the pulses falls too close the T-wave.

After the supranormal period 110, the heart tissue is sufficiently repolarized 114 and "alert", that is, the heart will respond to a stimulus. Hereinafter, the period following the supranormal period 110 shall be referred to as the "alert period" 114 of the cardiac cycle. The alert period 114 of the cardiac cycle corresponds to an alert period in a pulse generator's timing cycle wherein the pulse generator is "alert" to (i.e., able to sense) intrinsic R-waves and will respond to the absence of R-waves by eliciting a stimulation pulse which, because the heart is repolarized, is expected to capture the heart).

Figure 2:
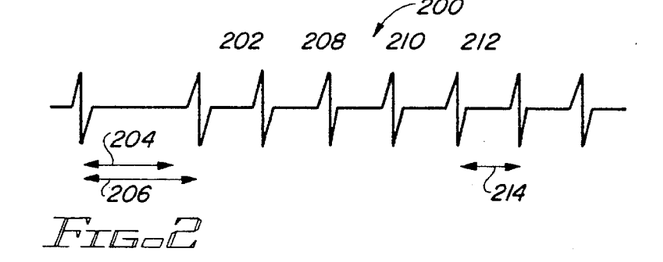
FIG. 2 is a timing waveform illustrating a confirmed tachycardia episode.
Figure 3:
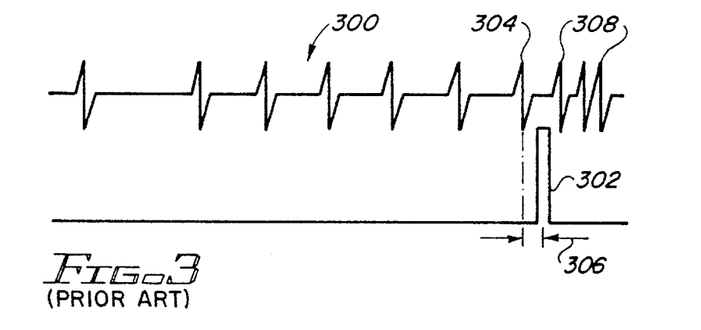
FIG. 3 is a timing waveform illustrating prior art synchronization of a cardioversion shock to an R-wave.
Figure 4:
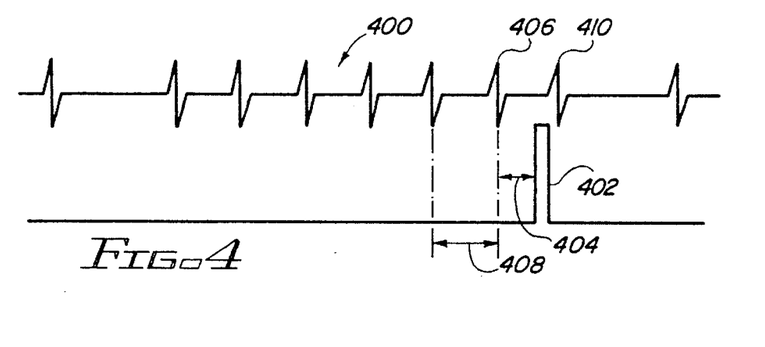
FIG. 4 is a timing waveform illustrating synchronization of a cardioversion shock to provide preemptive depolarization in accordance with the principles of the present invention.

Before presenting the implementation of the system, it will be helpful to understand the response of an implantable cardiac stimulating device to a tachycardia. For this reason, the timing waveforms of FIGS. 2–4 are described next. (While the cardiac signals shown in FIGS. 2–4 are described below as R-waves, the same mechanism would also be true in the atrium.)

In FIG. 2, a waveform 200 depicts a plurality of heartbeats representing a tachycardia episode in progress starting at a heartbeat 202. If each of a preprogrammed number of heartbeats occurs within a preprogrammed time interval 204 following its respective preceding heartbeat, tachycardia is confirmed and assumed to be in progress. A preprogrammed time interval 204 corresponds to a maximum allowable heart rate. The number of heartbeats and the preprogrammed time interval 204 may be programmed by a physician. In the waveform 200, the preprogrammed number of beats is five and the preprogrammed time interval 204 is slightly less than one normal heartbeat cycle 206. Here, tachycardia is confirmed to be in progress since each of four successive heartbeats 202, 208, 210, 212 occurred at times less than the preprogrammed time interval 204 of their preceding respective heartbeats and a time interval 214 following the fourth successive heartbeat 212 is less than the preprogrammed time interval 204.

In FIG. 3, a waveform 300 illustrates the application of a prior art "synchronous" cardioversion therapy to revert the tachycardia shown in the waveform 200 of FIG. 2. The underlying principle of this type of cardioversion shock therapy is that if a cardioversion shock is applied to the heart (not shown) at least once shortly after a heartbeat, the heart may revert back to sinus rhythm. A cardioversion shock 302 is electronically synchronized to fire at an R-wave 304 which is used to confirm tachycardia. Because of a short electronic time delay 306 inherent to device switching and charging requirements, the cardioversion shock 302 is generally provided many milliseconds after the R-wave 304. Typical delays are on the order of between about 20 milliseconds and about 40 milliseconds. The electronic time delay 306 is generally fixed, but can depend on the state of the pulse generator (not shown). It typically is not programmable by the physician nor does it provide for varying tachycardia rates. Thus, the coupling interval of shocks administered in the prior art "synchronous" cardioversion therapy systems are independent of heart rate. Despite the electronic time delay 306, the shock is typically administered while significant portions of the heart are still refractory from the detected depolarization. This lack of proper synchronization may produce afterdepolarizations, and perhaps an acceleration 308.

In FIG. 4, a waveform 400 illustrates delivery of cardioversion shock therapy in accordance with the principles of the present invention. A single cardioversion shock 402 is delivered at a time interval 404 which is expected to fall in the alert period following an R-wave 406 which is used to confirm a tachycardia. The time interval 404 can be a fixed time or a percentage of a tachycardia cycle length 408. With proper synchronization, the cardioversion shock 402 will have a high probability of creating an action potential that is conducted through the heart. Thus, unlike prior art "synchronized" systems, which are really post-arrhythmia systems that simply immediately deliver a cardioversion shock after tachycardia is confirmed, the present invention advantageously delays delivery of a cardioversion shock until the alert period 114 of the detected tachycardia cycle. By properly synchronizing the cardioversion shock 402 in this manner, the cardioversion shock 402 may arrest the tachycardia episode with much less energy. This provides a significant advantage over the prior art "synchronous" cardioversion therapy systems—the use of less energy both reduces the discomfort to the patient and increases the useful life of the implantable cardiac stimulating device (not shown). The latter advantage is particularly significant considering the fact that replacing the power source in an implantable cardiac stimulating device requires a surgical procedure. Additionally, the incidence of acceleration to a faster, more dangerous heart rate may be reduced.

In accordance with this invention, the time interval 404 is programmable as either a fixed time delay or a percentage of the tachycardia cycle length 408. The preferred embodiment uses the percentage of the tachycardia cycle length 408, preferably in the range of 70–90%, however, the criteria could be as high as 30–99%. For example, the physician may select to have the cardioversion shock 402 provided at the time interval 404 which is equivalent to 90% of the tachycardia cycle length 408. If tachycardia was measured at 150 beats per minute (400 millisecond cycle length), then the cardioversion shock 402 would be provided 360 milliseconds (90% of 400) after the confirmation R-wave 406. In this fashion, the cardioversion shock 402 has a greater chance of advantageously preempting the next expected tachycardia beat (not shown) with an elicited beat 410. When this occurs, the heart may regain natural pacing control. In this embodiment, the system is thus heart rate dependent because the time interval 404 depends on a particular patient's tachycardia cycle length 408.

In an alternative embodiment, a fixed time interval could be selected. The preferred embodiment would allow a fixed time interval generally greater than 300 milliseconds. A value of 300 ms for the fixed time interval is preferred because it is generally believed that the majority of patients are no longer refractory after 300 ms. However, the fixed time interval could be completely programmable for the physician, with the possibility that some patients need (particularly at high rates) a value between 150 ms and the tachycardia cycle length. For example, the time interval 404 could be selected to be 350 milliseconds, independent of the tachycardia cycle length 406. When this method is used, the physician will typically have historical data from which to base the time interval 404. Regardless of the method of synchronization, the cardioverter is programmed to synchronize the cardioversion shock 402 so that it falls within the alert period 114 (FIG. 1) of the cardiac cycle associated with the tachycardia confirmation R-wave 406.

Figure 5:
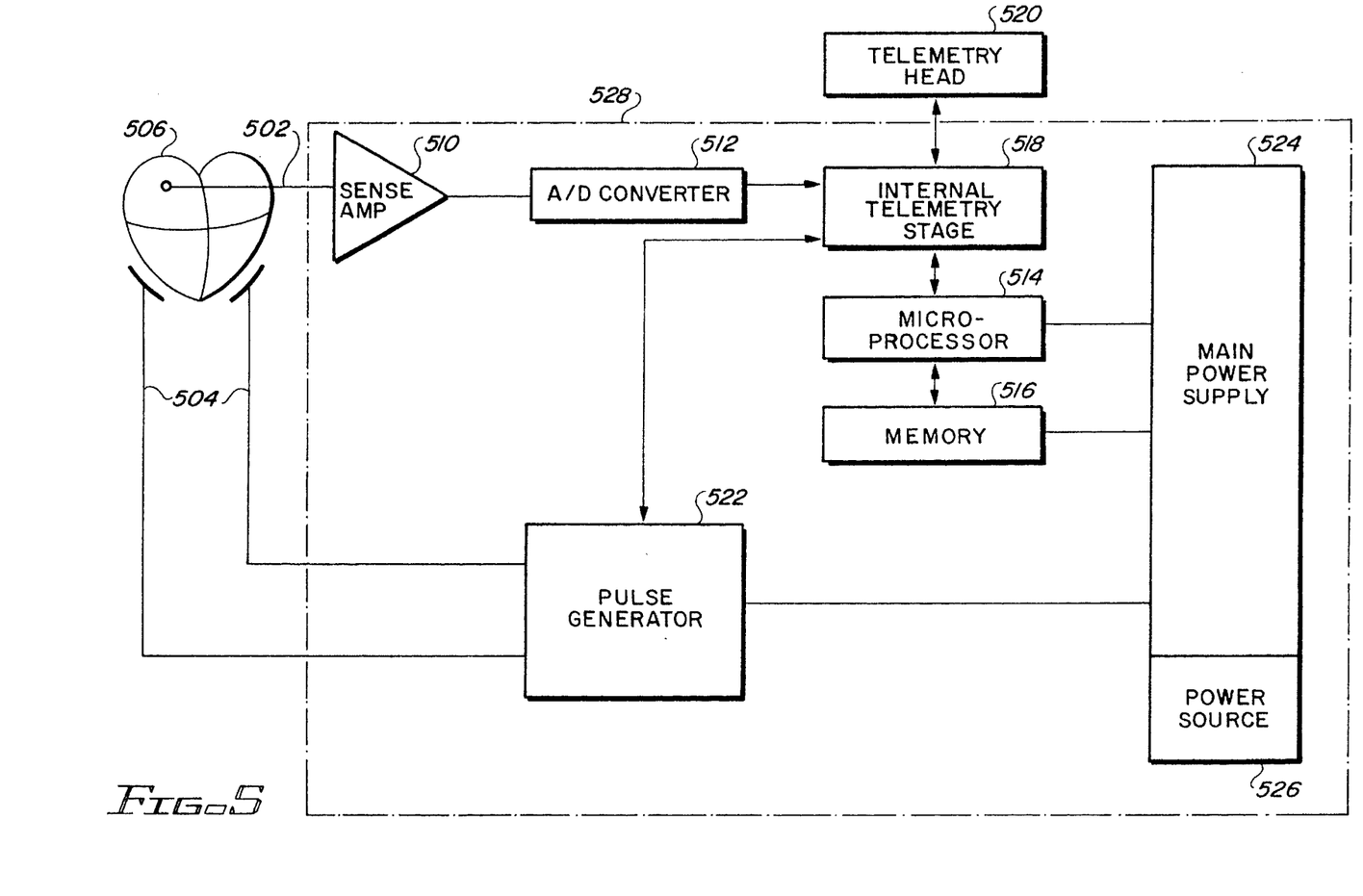
FIG. 5 is a schematic block diagram of a preferred embodiment of an implantable cardiac stimulating device designed to administer cardioversion shock therapy to provide preemptive depolarization in accordance with the principles of the present invention.

In FIG. 5, a block diagram of an implantable cardioversion shock system 500 designed to provide preemptive cardioversion shock therapy is described. The implantable cardioversion shock system 500 is designed to be implantable and includes a connectable cardiac sensing lead 502 and shocking electrodes 504. While the shocking electrodes 504 are shown as patch electrodes, they may in fact be any combination of patch, subcutaneous patch, or endocardial leads. The cardiac sensing lead 502 is physically connected to a patient's heart 506, and the implantable cardioversion shock system 500 also includes a sense amplifier 510 which receives electrical signals from the cardiac sensing lead 502 representing cardiac electrical activity. In an alternative embodiment, shocking and sensing functions may be provided by the same physical lead (not shown). The implantable cardioversion shock system 500 further includes an analog-to-digital converter 512 which converts the analog electrical signals provided by the sense amplifier 510 to digital signals suitable for digital logic devices.

A microprocessor 514 receives the digital signals from the analog-to-digital converter 512 and performs operations so as to generate different control and data outputs. Alternatively, other customized logic devices (not shown) can be used in place of the microprocessor 514. A memory 516, which is available to the microprocessor 514, stores program instructions and operating parameters. An internal telemetry stage 518 transmits and receives operating parameters between a telemetry head 520, which communicates with an external programmer (not shown) and the memory 516, via the microprocessor 514.

A pulse generator 522, responsive to the microprocessor 514, generates and stores the energy for cardioversion shocks. When the microprocessor 514 determines that it is necessary to administer cardioversion therapy, it sends a command to the pulse generator 522 causing it to generate and deliver a cardioversion shock to the heart 506 via the shocking electrodes 504.

The sense amplifier 510 and the analog-to-digital converter 512 may be combined into one or several integrated circuits (not shown). Similarly, the microprocessor 514 and the memory 516 may be combined into one integrated circuit (not shown).

A main power supply 524, including a power source 526, provides a reliable voltage and current source to the following active components within an implantable enclosure 528: the sense amplifier 510 (connection not shown), the analog-to-digital converter 512 (connection not shown), the microprocessor 514, the memory 516, the internal telemetry stage 518, and the pulse generator 522. The main power supply 524 also regulates and distributes appropriate voltage and current levels to all active components of the implantable cardioversion shock system 500. Energy is supplied to the main power supply 524 by the power source 526. The power source 526 is preferably a long life battery such as a lithium battery or a plurality of lithium batteries.

Many of the aforementioned elements are conventional and thus, little further description of their operation is necessary. Generally, the sense amplifier 510 measures the electrical activity of the heart 506 from the signals transmitted by the cardiac sensing lead 502. The sense amplifier 510 conditions the sensor signal to provide appropriate input to the analog-to-digital converter 512. The analog-to-digital converter 512 converts the analog signals from the sense amplifier 510 to digital signals suitable for input to the microprocessor 514. The microprocessor analyzes the data received from the analog-to-digital converter 512 and determines when to instruct the pulse generator 522 to generate and deliver a cardioversion shock to the heart 506 via the shocking electrodes 504. The previously discussed problem associated with charging and switching delays is typically not a problem in the context of the present invention, because such delays are normally of substantially shorter duration than the time between a confirmation R-wave and the delivery of the cardioversion shock (i.e., the time interval 404 of FIG. 4).

The telemetry head 520 is provided so that the physician can communicate with the microprocessor 514 via the internal telemetry stage 518. Both the telemetry head 520 and the internal telemetry stage 518 may include encoders (not shown), decoders (not shown), transmitters (not shown) and receivers (not shown) that are conventional for data communications. The internal telemetry stage 518 and the telemetry head 520 may utilize either radio frequency or magnetic impulse transmission or other suitable transmission means to allow the external programmer to enter operating parameter data in the memory 516, preferably by coded transmission. This advantageously allows the operating parameters, including the time interval 404, to be modified over the useful life of the device.

The electronic components of the implantable cardioversion shock system 500 are within the implantable enclosure 528 which is biologically compatible and hermetically sealed, such as one constructed of titanium. The implantable enclosure 528 itself is implanted at a suitable location in the patient's body (not shown).

Figure 6:
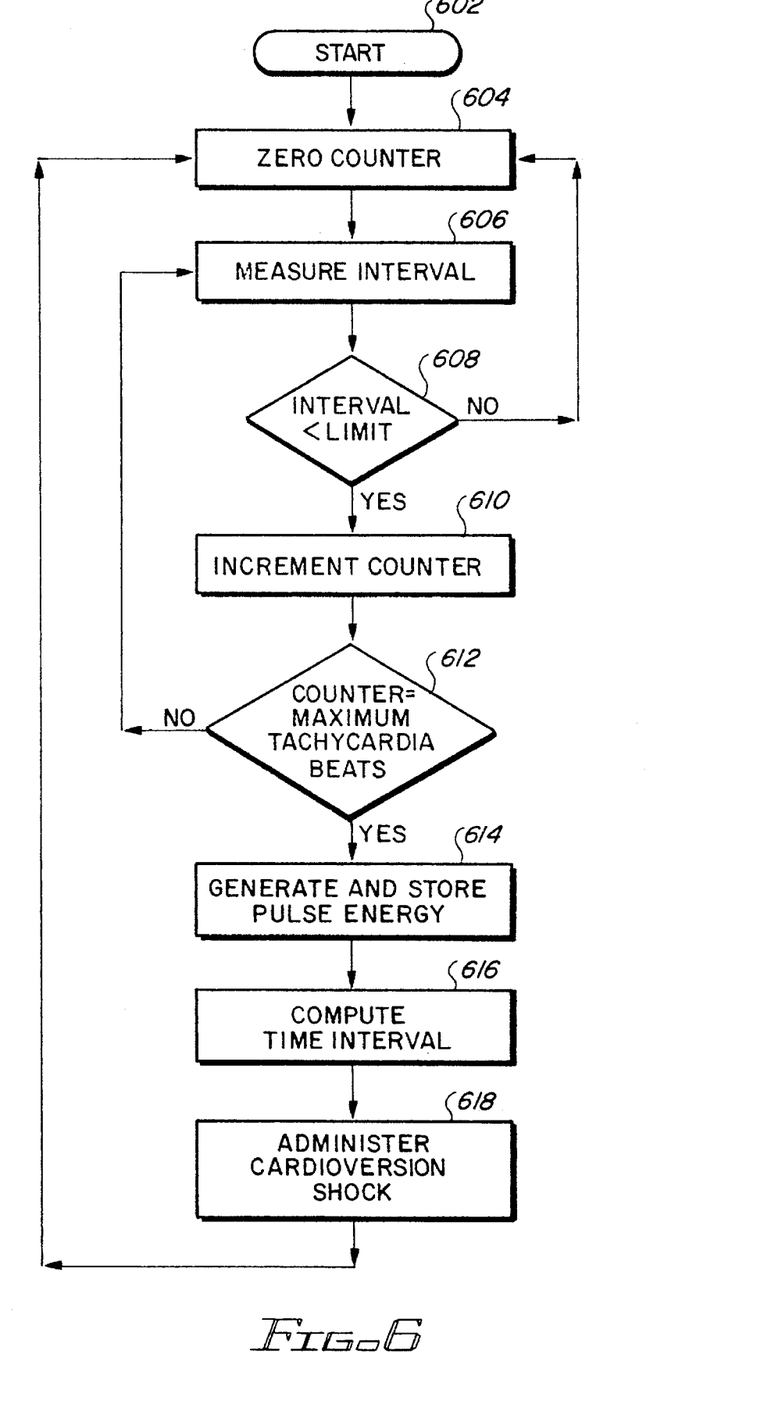
FIG. 6 is a logic flow diagram of software executed by the microprocessor shown in the diagram of FIG. 5.

In FIG. 6, a logic flow diagram of a control program for the microprocessor 514 of FIG. 5 is described, as it may be implemented in suitable microcode or any other higher level language. The preprogrammed number of heartbeats, which is the number of accelerated heartbeats used to confirm tachycardia, the time interval corresponding to the maximum heart rate (i.e., the time interval 204 of FIG. 2), the percentage of the tachycardia cycle length when the stimulation pulse will be applied (used to compute the time interval 404 of FIG. 4), the energy level of the stimulation pulse, and possibly other parameters, are set by the physician using an external programmer (not shown) via the internal telemetry stage 518 and the telemetry head 520 of FIG. 5.

The main program begins at start 602, which is followed by a step 604 at which a counter is set to zero. At a step 606 the time interval between two consecutive heartbeats is determined from data received from the analog-to-digital converter 512 (FIG. 5). At a test 608, the microprocessor 514 (FIG. 5) determines whether the interval measured in the step 606 is less than the time interval corresponding to the maximum heart rate (i.e., the preprogrammed time interval 204 of FIG. 2). If the interval measured at the step 606 is not less than the preprogrammed time interval 204 (FIG. 2), the program loops back to the step 604; otherwise, the counter is incremented at a step 610.

The step 610 is followed by a test 612 at which the microprocessor 514 (FIG. 5) determines whether the counter is equal to the preprogrammed number of heartbeats required to confirm tachycardia. If tachycardia is not confirmed, the program loops back to the step 606, where the time interval between the next two consecutive heartbeats is measured. The time required for the program to step through the loop beginning at the step 606, followed by the test 608, the step 610, the test 612, and returning back to the step 606 is insignificant as compared to the time between two successive heartbeats, so that the heartbeat intervals measured in the step 606 are from consecutive heartbeats, and no heartbeat intervals are skipped.

If tachycardia is confirmed at the test 612, the program proceeds to a step 614, where the microprocessor 514 (FIG. 5) directs the pulse generator 522 (FIG. 5) to generate and store the energy necessary for the cardioversion shock 402 (FIG. 4). The program then proceeds to a step 616 where the microprocessor 514 (FIG. 5) computes the time interval 404 (FIG. 4), which determines when the cardioversion shock 402 (FIG. 4) is applied. In the preferred embodiment, the time interval 404 (FIG. 4) is computed using the aforementioned preprogrammed percentage and the tachycardia cycle length measured at the step 606. At a step 618, the microprocessor 514 (FIG. 5) instructs the pulse generator 522 (FIG. 5) to administer the cardioversion shock 402 (FIG. 4) to the heart 506 (FIG. 5) via the cardioversion electrodes 504 (FIG. 5) after the time interval 404 (FIG. 4) determined at the step 616. The program then loops back to the step 604, where the counter is zeroed in preparation for response to another tachycardia episode.

An example of the operation of the microprocessor control program described with respect to FIG. 6 is now provided by reference to the waveform 200 of FIG. 2. At the heartbeat preceding the heartbeat 202 (FIG. 2), the counter value is zero. The previous normal heartbeats separated by time interval 206 (FIG. 2) would result in program flow proceeding from the step 604, to the step 606, to the test 608, and back to the step 604. The counter value would remain at zero. At the heartbeat 202 (FIG. 2), the interval measured is less than the normal heartbeat cycle 206 (FIG. 2), and the counter is incremented to a value of one at the step 610. At the test 612, it is determined that the counter value is less than the preprogrammed number of heartbeats, and the program loops back to the step 606. Following the heartbeats 208, 210, and 212 (FIG. 2), the counter is incremented to values of two, three, and four respectively. Program flow loops back from the test 612 to the step 606 after each counter increment. On the next heartbeat after the heartbeat 212 (FIG. 2), the counter is incremented to the value five. In this example, five equals the preprogrammed number of rapid heartbeats required to confirm tachycardia. Thus, the test 612 causes the program to proceed to the steps 614, 616, and 618 to deliver therapy. After therapy is delivered, the program loops back to the step 604 where the counter is set to zero, and subsequent heartbeat intervals are measured.

Thus an implantable cardiac stimulating device and method for administering synchronized cardioversion shock therapy is provided. One skilled in the art will appreciate that the present invention can be practiced by other than the described embodiments, which are presented for purposes of illustration and not of limitation, and the present invention is limited only by the claims that follow.

What is claimed is:

1. An implantable cardioversion shock therapy system, comprising:

sensing means for sensing intrinsic R-waves;

pulse generating means for generating a cardioversion shock and for delivering the cardioversion shock to cardiac tissue; and control means, responsive to the sensing means, for analyzing the R-waves to confirm a tachycardia episode, and for controlling the pulse generating means to trigger the cardioversion shock after a predetermined delay corresponding to a period when the cardiac tissue is repolarized, the predetermined delay being synchronized from a last R-wave following the confirmation of the tachycardia episode so that the cardioversion shock preempts a successive R-wave.

2. The system of claim 1, further comprising:

an external programming means for sending system operating parameters to and receiving data from the control means;

telemetry means, coupled to the control means, for receiving the system operating parameters, including the predetermined delay, from the external programming means.

3. The system of claim 1, wherein the control means further comprises:

means for defining the predetermined delay as a predetermined fixed time interval which is expected to occur when the cardiac tissue is repolarized.

4. The system of claim 3, wherein the predetermined fixed time interval is at least greater than 300 msec.

5. The system of claim 3, wherein:

the control means further includes means for determining a tachycardia cycle length; and the predetermined fixed time interval is a programmable value between 150 ms and the tachycardia cycle length.

6. The system of claim 1, wherein the control means further comprises:

means for determining a tachycardia cycle length; and means for defining the predetermined delay as a predetermined percentage of the tachycardia cycle length which is expected to occur when the cardiac tissue is repolarized.

7. The system of claim 6, wherein the predetermined percentage of the tachycardia cycle length is in the range of 30–99% of the tachycardia cycle length.

8. An implantable system for administering cardioversion shock therapy to cardiac tissue in accordance with a tachycardia rate of a patient to preempt an expected tachycardia beat, the system comprising:

sensing means for sensing intrinsic R-waves;

pulse generating means for generating a cardioversion shock and delivering the cardioversion shock to the cardiac tissue; and control means, responsive to the sensing means, for analyzing the intrinsic R-waves to determine a tachycardia cycle length, and for triggering the pulse generating means to deliver the cardioversion shock after a predetermined time, determined as a function of the tachycardia cycle length, has elapsed following a preceding tachycardia beat to elicit a heartbeat that preempts the expected tachycardia beat.

9. The system of claim 8, wherein the function of the tachycardia cycle length is a predetermined percentage of the tachycardia cycle length.

10. The system of claim 9, further comprising:

an external programming means for sending system operating parameters to and receiving data from the control means;

telemetry means, coupled to the control means, for receiving the system operating parameters, including the predetermined percentage, from the external programming.

11. An implantable cardioversion shock therapy system, comprising:

cardiac sensing means for sensing naturally occurring cardiac depolarizations in a selected chamber of a patient's heart;

pulse generator means for providing a cardioversion shock of sufficient energy to terminate a tachycardia episode in the selected chamber of the heart;

a shocking lead, coupled to the pulse generator means, for delivering the cardioversion shock to the selected chamber of the heart; and processing means, coupled to the cardiac sensing means and the pulse generator means, for confirming a tachycardia episode based on the sensed cardiac depolarizations and for controlling the pulse generator means to provide the cardioversion shock after a predetermined time interval following confirmation of the tachycardia episode to preempt an expected tachycardia beat.

12. The system of claim 11, wherein the processing means further comprises:

control means for defining the predetermined time interval as an alert interval corresponding to an expected alert period of the heart following the refractory period and prior to the next expected tachycardia beat.

13. The system of claim 12, wherein:

the processing means includes means for determining a tachycardia cycle length; and the control means includes means for defining the predetermined time interval as a predetermined percentage of the tachycardia cycle length following a preceding tachycardia beat.

14. The system of claim 13, wherein the predetermined percentage of the tachycardia cycle length is in the range of 30–99% of the tachycardia cycle length.

15. The system of claim 11, wherein the control means further comprises:

means for defining the predetermined time interval as a predetermined fixed time interval, triggered from a preceding tachycardia beat, which is expected to occur when the cardiac tissue is repolarized.

16. The system of claim 15, wherein:

the control means further includes means for determining a tachycardia cycle length; and the predetermined fixed time interval is a programmable value between 150 ms and the tachycardia cycle length.

17. An implantable cardioversion shock therapy system, comprising:

means for detecting a tachycardia episode;

means for delivering a cardioversion shock to cardiac tissue in response to the tachycardia episode; and means for delaying delivery of the cardioversion shock by a predetermined time interval measured from a preceding tachycardia beat and preemptively before an expected tachycardia beat.

18. A method of providing cardioversion shock therapy to cardiac tissue, comprising the steps of:

detecting a tachycardia episode; and delivering a cardioversion shock after a predetermined delay period corresponding to a period between a preceding tachycardia beat and an expected tachycardia beat when the cardiac tissue is non-refractory following detection of the tachycardia episode.

19. The method of claim 18, wherein the delaying step comprises the step of:

delivering the cardioversion shock after a predetermined fixed time interval following the preceding tachycardia beat has elapsed.

20. The method of claim 18, wherein the delaying step comprises the steps of:

determining a tachycardia cycle length; and delivering the cardioversion shock after a length of time corresponding to a predetermined percentage of the tachycardia cycle length has elapsed following the preceding tachycardia beat.

21. The method of claim 18, wherein the detecting step comprises the step of:

detecting a ventricular tachycardia episode.

22. The method of claim 18, wherein the detecting step comprises the step of:

detecting an atrial tachycardia episode.

23. A method of administering cardioversion shock therapy to cardiac tissue to preempt an expected tachycardia beat, comprising the steps of:

detecting an occurrence of a tachycardia episode;

determining a tachycardia cycle length of the tachycardia episode; and delivering a cardioversion shock to the cardiac tissue after a length of time, determined as a function of preceding tachycardia beat so that the cardioversion shock is delivered when the cardiac tissue is repolarized.

24. The method of claim 23, wherein the function of the tachycardia cycle length is a predetermined percentage of the tachycardia cycle length.

25. An implantable cardioversion shock therapy system, comprising:

sensing means for sensing intrinsic P-waves;

pulse generating means for generating a cardioversion shock and for delivering the cardioversion shock to cardiac tissue; and control means, responsive to the sensing means, for analyzing the P-waves to confirm an atrial tachycardia episode, and for controlling the pulse generating means to trigger the cardioversion shock after a predetermined delay, corresponding to a period when the cardiac tissue is repolarized, the predetermined delay being synchronized from a last P-wave following the confirmation of the atrial tachycardia episode so that the cardioversion shock preempts a successive P-wave.

26. The system of claim 25, further comprising:

an external programming means for sending system operating parameters to and receiving data from the control means;

telemetry means, coupled to the control means, for receiving the system operating parameters, including the predetermined delay, from the external programming means.

27. The system of claim 25, wherein the control means further comprises:

means for defining the predetermined delay as a predetermined fixed time interval which is expected to occur when the cardiac tissue is repolarized.

28. The system of claim 27, wherein the predetermined fixed time interval is at least greater than 300 msec.

29. The system of claim 27, wherein:

the control means further includes means for determining a tachycardia cycle length; and the predetermined fixed time interval is a programmable value between 150 ms and the tachycardia cycle length.

30. The system of claim 25, wherein the control means further comprises:

means for determining a tachycardia cycle length; and means for defining the predetermined delay as a predetermined percentage of the tachycardia cycle length which is expected to occur when the cardiac tissue is repolarized.

31. The system of claim 30, wherein the predetermined percentage of the tachycardia cycle length is in the range of 30–99% of the tachycardia cycle length.

\* \* \* \* \*